US012685728B2

(12) United States Patent
Vyas

(10) Patent No.: US 12,685,728 B2
(45) Date of Patent: Jul. 21, 2026

(54) ANTI-VERTIGO COMPOUND AND PHARMACEUTICAL COMPOSITIONS THEREOF

(71) Applicant: Amneal Pharmaceuticals LLC, Bridgewater, NJ (US)

(72) Inventor: Nirav Vyas, Ahmedabad (IN)

(73) Assignee: AMNEAL PHARMACEUTICALS LLC, Bridgewater, NJ (US)

( * ) Notice: Subject to any disclaimer, the term of this patent is extended or adjusted under 35 U.S.C. 154(b) by 566 days.

(21) Appl. No.: 18/033,993

(22) PCT Filed: Sep. 10, 2021

(86) PCT No.: PCT/IN2021/050886
§ 371 (c)(1),
(2) Date: Apr. 26, 2023

(87) PCT Pub. No.: WO2022/091118
PCT Pub. Date: May 5, 2022

(65) Prior Publication Data

US 2023/0390271 A1 Dec. 7, 2023

(30) Foreign Application Priority Data

Oct. 28, 2020 (IN) ............................ 202021047025

(51) Int. Cl.
*A61K 31/4453* (2006.01)
*A61K 9/00* (2006.01)
*A61P 1/08* (2006.01)

(52) U.S. Cl.
CPC ........ *A61K 31/4453* (2013.01); *A61K 9/0053* (2013.01); *A61P 1/08* (2018.01)

(58) Field of Classification Search
CPC .................................................. A61K 31/4453
See application file for complete search history.

(56) References Cited

U.S. PATENT DOCUMENTS

2009/0176792 A1 7/2009 Gant et al.

FOREIGN PATENT DOCUMENTS

| | | | |
|---|---|---|---|
| EP | 0385491 A1 | | 9/1990 |
| EP | 0894794 A1 | | 2/1999 |
| WO | 2019004953 A1 | | 1/2019 |
| WO | WO 2019/004953 | * | 1/2019 |

OTHER PUBLICATIONS

Zoic's ASTARIL-LR.*
International Search Report dated Dec. 29, 2021, for corresponding International Patent Application No. PCT/IN2021/050886.
Written Opinion dated Dec. 29, 2021, for corresponding International Patent Application No. PCT/IN2021/050886.
Aliprandi et al., (2002). "Therapeutic Use of Levocloperastine as an Antitussive Agent: An Overview of Preclinical Data and Clinical Trials in Adults and Children." Clinical Drug Investigation. 22. 209-220.
Dyhrfjeld-Johnsen et al., (2019) "Management of peripheral vertigo with antihistamines: New options on the horizon." Br J Clin Pharmacol. 85. 2255-2263.

* cited by examiner

*Primary Examiner* — Rei Tsang Shiao
(74) *Attorney, Agent, or Firm* — Troutman Pepper Locke LLP

(57) ABSTRACT

The present invention relates to uses of Levocloperastine for the treatment or prevention of vertigo, disease associated with vertigo or symptoms associated therewith. Further, the invention also relates to oral pharmaceutical composition comprising Levocloperastine and one or more pharmaceutical excipients and its preparation process.

15 Claims, No Drawings

ANTI-VERTIGO COMPOUND AND PHARMACEUTICAL COMPOSITIONS THEREOF

This application is a National Stage Application under 35 U.S.C. § 371 of PCT International Application No. PCT/IN2021/050886, filed on Sep. 10, 2021, which claims priority to Indian Patent Application No. IN 202021047025, filed Oct. 28, 2020, all of which are hereby incorporated by reference herein in their entireties.

FIELD OF THE INVENTION

The present invention relates to method of treatment of vertigo and/or one or more symptoms of vertigo or diseases associated with vertigo using levocloperastine. The invention, further relates to composition comprising Levocloperastine and use thereof for the treatment or prevention of one or more symptoms of vertigo or diseases associated with vertigo.

BACKGROUND OF THE INVENTION

Levocloperastine (I) is levorotatory isomer of DL-cloperastine. Levocloperastine is used in reducing the intensity and frequency of cough. The antihistamine, antiserotonergic and muscle-relaxant properties of Levocloperastine contribute to its overall efficacy in the treatment of cough, bronchospasm and related symptoms

Figure 1

(I)

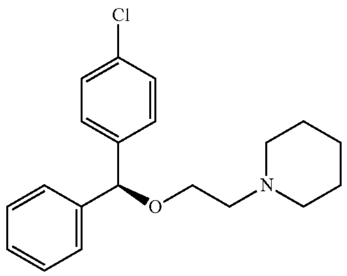

Peripheral vertigo is an abnormality of integration mechanisms of information in the central nervous system resulting from rapid dysfunction of equilibrium nervous system occurring in a vestibular nervous system and it is accompanied with various symptoms such as dysesthesia of motion and position, nystagmus, dysequilibrium, head deviation, nausea, vomiting, sweating, salivation and tachycardia. The percentage of people with Peripheral vertigo is increasing.

The most common causes of Peripheral vertigo are inner ear infections or diseases of the ear such as benign paroxysmal positional Peripheral vertigo (BPPV), vestibular neuritis, and Meniere's disease. BPPV can occur when calcium builds up in canals of the inner ear, causing brief dizziness that lasts from 20 seconds to one minute. It is usually brought on by trauma to the head or by moving the head in certain positions. Vestibular neuritis is brought on by an inner ear infection that causes inflammation around the nerves that help the body sense balance. It results in a severe bout of Peripheral vertigo that can last a day or more and sometimes includes hearing loss. Meniere's disease (MD) is a disorder of the inner ear that is characterized by episodes of feeling like the world is spinning (Peripheral vertigo), ringing in the ears (tinnitus), hearing loss, and a fullness in the ear.

Meclizine, diphenhydramine, scopolamine, diazepam, lorazepam, betahistine, and cinnarizine are commonly used medications for Peripheral vertigo, and the current anti-Peripheral vertigo drugs cause drowsiness. Further, a faster onset of action is also preferable for Peripheral vertigo patients.

There exists a need for an effective vertigo treatment or diseases associated with vertigo that would avoid drowsiness and that would relieve the vegetative symptoms in shorter duration of time period and provide a faster onset of action. Major patients suffering from Peripheral vertigo need an effective treatment which can provide relief from Peripheral vertigo and vegetative concomitant symptoms like nausea, vomiting, sweating, tachycardia. The present invention provides best patient compliance by providing quick relief in shorter duration of time without sedation to patients.

OBJECTS OF THE INVENTION

The primary object of the present invention is to provide treatment of vertigo and/or prevention of one or more symptoms of vertigo or disease associated with Vertigo using levocloperastine.

Another object of the present invention is to provide a treatment and quick relief for one or more symptoms of peripheral vertigo using Levocloperastine.

Another object of the present invention is to use Levocloperastine for the treatment for vertigo or clinical sign and symptom associated with vertigo.

Another object of the present invention is to use Levocloperastine for the treatment of vertigo or clinical sign and symptom or vegetative concomitant symptoms associated with vertigo, or disease associated with Vertigo within a shorter duration of time as compared to standard of care therapy used.

Another object of the present invention is to provide a pharmaceutical composition for use in the treatment of vertigo or clinical sign and symptoms associated with it or vegetative concomitant symptoms within a shorter duration of time as compared to standard of care therapy.

Another object of the present invention is to provide a pharmaceutical composition of Levocloperastine and use thereof for the treatment or prevention of one or more symptoms of vertigo.

SUMMARY OF INVENTION

One embodiment of the invention is to use Levocloperastine for the treatment of vertigo and/or prevention of one or more symptoms of vertigo.

Another embodiment of the invention is to use Levocloperastine for the treatment of Peripheral vertigo and clinical sign and symptoms of Peripheral vertigo.

Another embodiment of the invention is administration of therapeutically effective dose of Levocloperastine for the treatment of vertigo and/or one or more symptoms of vertigo.

Another embodiment of the invention is administration of therapeutically effective dose of Levocloperastine for the treatment of peripheral vertigo.

Another embodiment of the invention is use of Levocloperastine for quicker relief of vertigo symptoms compared to existent standard of care and also prompt relief of associated vegetative concomitant symptoms and in turn contributing to a major extent towards treating patients with vertigo plus increasing compliance of these patients.

Another embodiment of the invention is a novel pharmaceutical composition comprising Levocloperastine for use in the treatment of vertigo or one or more symptom associated with vertigo.

Another embodiment of the invention is to use Levocloperastine for the treatment of vertigo or one or more symptom associated with vertigo or vegetative concomitant symptoms or disease associated with it, within a shorter duration of time as compared to standard of care therapy used.

Another embodiment of the invention is, method of treatment of vertigo and/or prevention of one or more symptoms of vertigo or disease associated with vertigo in a human subject, wherein the method comprises administering to the subject, a therapeutically effective amount of Levocloperastine or a pharmaceutically acceptable salt thereof for a duration of time that is shorter as compared to standard of care therapy used.

Another embodiment of the invention is a pharmaceutical composition for use in the treatment of vertigo or diseases associated with vertigo or vegetative concomitant symptoms within a shorter duration of time as compared to standard of care therapy used for treatment of vertigo or disease associated with vertigo.

DETAILED DESCRIPTION OF THE INVENTION

The above general and further specific embodiments of the invention including the examples, described hereinafter, are exemplary and in no way limits the scope of the inventions to expressly or specifically disclosed embodiments only; and variations and/or modifications thereof that are apparent to and obvious for a person skilled in the art are also included within the scope of the invention.

Unless otherwise defined, all the technical and scientific terms used herein shall bear the meaning as ordinarily understood by a person skilled in the field of the invention.

Processes, methods and techniques, which are commonly used and routinely practiced in the field of the invention and/or easily understood by a person skilled in the art, are not described in detail, for the sake of brevity.

The term "Levocloperastine" used throughout the specification includes the free base form and pharmaceutically acceptable salts thereof; anhydrous forms, solvates, hydrates and co-crystalline forms thereof; and crystalline and amorphous polymorphic forms thereof.

The term "Patient or subject" means a human being in some diseased state.

The term "Pharmaceutical composition" for the purpose of the invention, means a composition in the form of tablet, capsule, solution and suspension. The said pharmaceutical composition comprises of Levocloperastine and one of more pharmaceutically acceptable excipients.

One embodiment of the invention is, use of Levocloperastine or a pharmaceutically acceptable salt thereof, for the treatment of vertigo and/or prevention of one or more symptoms of vertigo.

Another embodiment of the invention is use of Levocloperastine or a pharmaceutically acceptable salt thereof, for the treatment of and/or prevention of one or more symptoms of vertigo or disease associated with vertigo. The vertigo associated disease includes but not limited to Meniere's disease and Giddiness.

Another embodiment of the present invention is to use Levocloperastine for the treatment of peripheral vertigo.

Another embodiment of the invention is use of Levocloperastine or a pharmaceutically acceptable salt thereof, in the preparation of a pharmaceutically acceptable composition for use in the treatment of vertigo and/or prevention of one or more symptoms of vertigo.

Another embodiment of the invention is administration of Levocloperastine or a pharmaceutically acceptable salt thereof at a therapeutically effective dose for the treatment of vertigo and/or prevention of one or more symptoms of vertigo.

Another embodiment of the invention is method of treatment of vertigo and/or prevention of one or more symptoms of vertigo or disease associated with Vertigo in a human subject, wherein the method comprises administering to the subject, a therapeutically effective amount of Levocloperastine or a pharmaceutically acceptable salt thereof.

Another embodiment of the invention is method of treatment of Peripheral Vertigo, Meniere's disease, Tinnitus, Hearing loss, Giddiness, Dysesthesia of motion and position, Nystagmus, Dysequilibrium, Dizziness, Head deviation, Nausea, Vomiting, Sweating, Salivation and Tachycardia, Dysstasia and Walking unsteadiness, Staggering, Rotary sensation, Tendency to fall, Lift sensation, Blackout, Change of position (lying), Bowing, Getting up, driving, Head movements (inclination, twist), eye movement or one or more symptoms or disease associated with it in a human subject, wherein the method comprises administering to the subject, a therapeutically effective amount of Levocloperastine or a pharmaceutically acceptable salt thereof.

Another embodiment of the invention is to use Levocloperastine in the treatment of vertigo and/or prevention of one or more symptoms of vertigo or diseases associated with vertigo in a human subject.

Another embodiment of the invention is to use Levocloperastine in the preparation of a pharmaceutical composition for use in the treatment of vertigo and/or prevention of one or more symptoms of vertigo or diseases associated with vertigo in a human subject.

Levocloperastine can be used at a daily dose of 5 to 1000 mg, preferably at a daily dose of about 5 to 500 mg, more preferably at a daily dose of about 5 to 200 mg, or more preferably at a daily dose of about 5-160 mg for the treatment or prevention of vertigo or disease associated with vertigo.

The daily dosage of Levocloperastine can be administered as a single dose or multiple divided doses.

The daily dosage of Levocloperastine can be administered as about 5-80 mg once daily, or as about 5-40 mg twice a day, or as about 3-30 mg thrice a day.

The daily dosage of Levocloperastine can be administered as about 60-90 mg once daily, or as about 30-45 mg twice a day, or as about 20-30 mg thrice a day.

The daily dosage of Levocloperastine can be administered as about 70-120 mg once daily, or as about 35-60 mg twice a day, or as about 25-40 mg thrice a day.

The daily dosage of Levocloperastine can be administered as about 90-160 mg once daily, or as about 45-80 mg twice a day, or as about 30-55 mg thrice a day.

The actual dosage of Levocloperastine can be calculated and adjusted according to the pharmaceutically acceptable salt thereof used. e.g. 35.4 mg of Levocloperastine Fendizoate is equivalent to 20 mg of Levocloperastine HCl.

Another embodiment of the invention is to use about 20-36 mg Levocloperastine or a pharmaceutically acceptable salt thereof three times a day for the treatment of vertigo or and/or prevention of one or more symptoms of vertigo.

Another embodiment of the invention is to use about 30-55 mg Levocloperastine or a pharmaceutically acceptable salt thereof twice a day for the treatment of vertigo or and/or prevention of one or more symptoms of vertigo.

Another embodiment of the invention is to use about 60-110 mg Levocloperastine or a pharmaceutically acceptable salt thereof once a day for the treatment of vertigo or and/or prevention of one or more symptoms of vertigo.

Another embodiment of the invention is to use about 30-55 mg Levocloperastine or a pharmaceutically acceptable salt thereof three times a day for the treatment of vertigo or and/or prevention of one or more symptoms of vertigo.

Another embodiment of the invention is to use about 45-85 mg Levocloperastine or a pharmaceutically acceptable salt thereof twice a day for the treatment of vertigo or and/or prevention of one or more symptoms of vertigo.

Another embodiment of the invention is to use about 90-160 mg Levocloperastine or a pharmaceutically acceptable salt thereof once a day for the treatment of vertigo or and/or prevention of one or more symptoms of vertigo.

Another embodiment of the invention is use of Levocloperastine for the treatment or prevention of vertigo or disease associated with vertigo, wherein vertigo symptoms scale of patients is 0 to 5.

Effectiveness of Levocloperastine in the treatment or prevention of vertigo or disease associated with vertigo has been evaluated as Improvement in vertigo symptoms based on MVS score as primary efficacy end point Improvement in quality of life (QoL) associated with Peripheral vertigo evaluated based on NVI and IGA score by means of a 5-point verbal rating scale (very much improved, much improved, slightly improved, not improved, deteriorated) rated by Investigator, Improvement in the severity of tinnitus assessed subjectively by THI on a categorical 3-point scale (yes/no/sometimes), and Improvement in four vegetative concomitant symptoms (nausea, vomiting, sweating, and tachycardia) based on their intensities evaluated by subjective 5-point VAS (0: not present; 1: moderate; 2: medium; 3: strong; 4: very strong).

The MVS score, a 12-item composite score to measure the severity of vertigo symptoms, is defined as the mean intensity of 6 (unprovoked) vertigo symptoms (dysstasia and walking unsteadiness, staggering, rotary sensation, tendency to fall, lift sensation, blackout) and vertigo in consequence of 6 triggering factors [change of position (lying), bowing, getting up, driving by car/train, head movements (inclination, twist), eye movement]. The intensity of each of the 12 single symptoms is rated by the patients by means of a 5-point VAS (0=not present, 1=moderate, 2=medium, 3=strong, 4=very strong). A mean MVS serving as a measure of vertigo intensity, will be calculated by adding the scores on all 12 vertigo symptoms and dividing by 12. The scale is rated by patients directly.

NVI is a 28-item questionnaire with a five-point Likert scale for each question (1: Never; 2: Rarely; 3: Sometimes; 4: Very often; 5: Always), for a total score ranging from 28 to 140 points. Higher scores indicate greater dysfunction. It assesses seven domains of cognition: space perception, attention, time perception, memory, emotional, visual/oculomotor, and motor. The scale is rated by patients.

Method of measurement for severity of tinnitus will be subjective evaluation by 25-item questions of THI on a categorical 3-point scale (yes/no/sometimes). The total score reflects the sum of all responses with a maximum score of 100 indicating the greatest impact on everyday function.

The CNS activity of Levocloperastine is highly selective; therefore, it avoids central adverse effects such as sedation. Levocloperastine, at doses up to 450-fold higher than the therapeutic doses, did not induce any clinically relevant sedation. Levocloperastine provides a faster onset of action and also avoids adverse events such as sedition and excitement. As treatment with Levocloperastine is not associated with any sedation, none of the symptoms associated with vertigo would be masked and surprisingly, levocloperastine, even without any sedative property, shows improvement in vertigo and vegetative concomitant symptoms associated with vertigo.

Levocloperastine provides the treatment of Vertigo or Peripheral vertigo or disease associated with vertigo or vegetative concomitant symptoms, within a shorter duration of time as compared to standard of care therapy used. Levocloperastine achieves comparable improvement in MVS score with a shorter duration of treatment compared to the standard of care treatment. The comparable amount of improvement in Vegetative concomitant symptoms severity is achieved by the standard of care treatment after about 28 days of treatment, is achieved by Levocloperastine in a treatment of duration of as short as about 7 days only, i.e. a remarkable reduction of the duration of the treatment to about $1/4^{th}$ of the standard of care treatment. Levocloperastine gives quick relief to Vertigo or its symptoms and improvement in severity of vegetative concomitant symptoms associated therewith.

The faster onset of action and shorter duration of treatment, without causing clinically relevant sedation of Levocloperastine aids in better patient compliance, better treatment adherence and limited motor/movement restrictions for the patients.

Another embodiment of the invention is method of treatment of Vertigo and/or prevention of one or more symptoms of Vertigo or vegetative concomitant symptoms or disease associated with Vertigo in a human subject, wherein the method comprises administering to the subject, a therapeutically effective amount of Levocloperastine or a pharmaceutically acceptable salt thereof for a duration of time that is shorter as compared to standard of care therapy used.

Another embodiment of the invention is to use a therapeutically effective amount of Levocloperastine or a pharmaceutically acceptable salt thereof for the treatment of Peripheral Vertigo, Meniere's disease, Tinnitus, Hearing loss, Giddiness, Dysesthesia of motion and position, Nystagmus, Dysequilibrium, Dizziness, Head deviation, Nausea, Vomiting, Sweating, Salivation and Tachycardia, Dysstasia and Walking unsteadiness, Staggering, Rotary sensation, Tendency to fall, Lift sensation, Blackout, Change of position (lying), Bowing, Getting up, driving, Head movements (inclination, twist), eye movement or one or more symptoms or disease associated with it for a duration of time that is shorter as compared to standard of care therapy used.

Another embodiment of the present invention is a pharmaceutical composition for use in the treatment of vertigo or diseases associated with vertigo or vegetative concomitant symptoms within a shorter duration of time as compared to standard of care therapy used for treatment of vertigo or disease associated with vertigo.

Another embodiment of the invention a pharmaceutical composition comprising Levocloperastine or pharmaceutically acceptable salt thereof for use in the treatment of vertigo and/or prevention of one or more symptoms of vertigo or disease associated with Vertigo in a human subject.

The pharmaceutically acceptable composition of Levocloperastine can be suitable for oral, buccal, sublingual, transdermal, intravenous, intraperitoneal, intramuscular or subcutaneous administration.

Another embodiment of the invention is an oral pharmaceutical composition comprising Levocloperastine for use in the treatment or prevention of vertigo or disease associated with vertigo.

Another embodiment of the invention is an oral pharmaceutical composition comprising Levocloperastine for use in the treatment or prevention of Peripheral vertigo or disease associated with Peripheral vertigo.

Another embodiment of the invention is a pharmaceutical composition comprising Levocloperastine for use in the treatment of vertigo and/or prevention of one or more symptoms of vertigo.

The pharmaceutical dosage form for use in the treatment or prevention of vertigo or disease associated with vertigo can be, but not limited to, a solid or liquid oral dosage form. The solid oral dosage form can be, but not limited to, tablet, capsule, granules or powder; and the liquid oral composition can be, but not limited to, solution, syrup, suspension or emulsion.

Another embodiment of the present invention is to use Levocloperastine for the treatment or prevention of vertigo or disease associated with vertigo, wherein the pharmaceutical composition used for the treatment or prevention of vertigo or disease associated with vertigo comprises Levocloperastine and one or more pharmaceutically acceptable excipients, wherein the said composition is in the form of liquid dosage form, wherein the said liquid dosage form is used for administration to paediatric as well as adult patients.

Another embodiment of the present invention is, Levocloperastine for the treatment of vertigo or disease associated with vertigo be used in admixture with conventional pharmaceutically acceptable carriers or diluents which are suitable for oral or parenteral administration.

Another embodiment of the present invention is, a stable oral pharmaceutical composition of Levocloperastine and one or more pharmaceutically acceptable excipients wherein the said composition is in tablet, capsule, solution, syrup or suspension dosage form.

Another embodiment of the present invention is, a stable oral pharmaceutical composition of Levocloperastine and one or more pharmaceutically acceptable excipients wherein the said pharmaceutically acceptable excipients comprising, but not limited to, diluent, disintegrants, binder, lubricants, anti-adherents, plasticizer, colouring agent, opacifier, chelating agents, glidant, flavouring agent, sweetening agent, coating agent, wetting agents, buffering agent, suspending agents, preservatives, surfactants, viscosity-modifying agents, tonicity adjusting agent, anti-dusting agents, adsorbents, antioxidants, humectant, solvents, polymers, soft gel capsule, hard gel capsule or mixture thereof.

The diluents or fillers can be selected from a group comprising but not limited to Lactose Monohydrate, Maize Starch, mannitol, dibasic calcium phosphate anhydrous, microcrystalline cellulose, Silicified MCC, corn starch, sucrose or other sugar or sugar derivatives, low substituted HPC, pregelatinized starch or mixture thereof, more preferably mannitol and microcrystalline cellulose. The fillers or diluents can be present in a concentration of from about 20% to about 80% by weight of the total weight of the composition.

The binder can be selected from a group comprising but not limited to pregelatinized starch, polyvinylpyrrolidone, Vinylpyrrolidone-vinyl acetate copolymer, povidone, copovidone, hydroxypropyl methyl cellulose, hydroxypropyl cellulose, maize starch, microcrystalline cellulose or mixture thereof. The binder can be present in a concentration of from about 0.5% to about 5% by weight of the total weight of the composition.

The disintegrant can be selected from a group comprising but not limited to crosscarmellose sodium, crospovidone, sodium starch glycolate, starch, corn starch, pregelatinized starch or mixture thereof. The disintegrant can be present in a concentration of from about 1% to about 10% by weight of the total weight of the composition.

The lubricant can be selected form the group comprising of agar, calcium stearate, ethyl oleate, ethyl laureate, glycerin, glyceryl palmitostearate, hydrogenated vegetable oil, magnesium oxide, magnesium stearate, sodium stearyl, sorbitol, stearic acid, talc, and zinc stearate or mixture thereof. The lubricant can be present in a concentration of from about 0.2% to about 2% by weight of the total weight of the composition.

The plasticizer can be selected from a group comprising Acetyltributyl Citrate, Acetyltriethyl citrate, Benzyl Benzoate, Chlorobutanol, Cellulose acetate phthalate compatible, Dextrin, Dibutyl Phthalate, DibutylSebacate, Diethyl Phthalate, Dimethyl Phthalate, Glycerin, Glycerinmonostearate, Hypromellose phthalate compatible, Mannitol, Mineral Oil and Lanolin Alcohols, Petrolatum and Lanolin Alcohols, Polyethylene Glycol, Propylene Glycol, Pyrrolidone, Sorbitol, Triacetin, Tributyl Citrate, Triethyl Citrate, Palmitic acid, Polymethacrylate compatible, Polyvinyl acetate phthalate, Stearic acid, Triethanolamine or mixture thereof.

The colouring agent can be selected from a group comprising Red 3 (Erythrosine), Red 40 (Allura red AC), Yellow 5 (Tartrazine), Yellow 6 (Sunset Yellow), Blue 1 (Brilliant Blue), Blue 2 (Indigotine), Green 3 (Fast Green), Iron Oxides or mixture thereof.

The opacifier can be selected from a group comprising AluminumMonostearate, Calcium Carbonate, Calcium Silicate, Ceresin, Titanium Dioxide, Zinc Acetate, Coloring agents, Ethylene glycol palmitostearate, Octyldodecanol, Zinc stearate or mixture thereof.

The chelating agents can be selected from a group comprising Calcium Acetate, HydroxypropylBetadex, Potassium Citrate, Citric acid, Citric Acid Monohydrate, Disodium Edetate, Edetic Acid, Malic Acid, Pentetic Acid, Phosphoric acid, Sodium Citrate Dihydrate, Dibasic Sodium Phosphate, Monobasic Sodium Phosphate, Tartaric Acid, Potassium citrate, Fumaric acid, Maltol, Pentetic acid or mixture thereof.

The glidant can be selected from a group comprising colloidal silicon dioxide, magnesium silicate, starch, talc, tribasic calcium phosphate, stearic acid, palmitic acid, polyethylene glycol, carnauba wax or mixtures thereof. The glidant can be present in a concentration of from about 0% to about 2% by weight of the total weight of the composition.

The flavouring agent can be selected from a group comprising Adipic Acid, n-butyl lactate, Confectioner's sugar, Citric Acid Monohydrate, Dibutylsebacate, Denatonium Benzoate, Ethyl Acetate, Ethyl Lactate, Ethyl Maltol, Ethyl Vanillin, Ethylcellulose, Fructose, Fumaric Acid, Leucine, Malic Acid, Maltol, Menthol, Methionine, Monosodium Glutamate, NeohesperidinDihydrochalcone, Neotame, Sodium Acetate, Sodium Lactate, Triethyl citrate, Tartaric Acid, Thaumatin, Thymol, Trehalose, Vanilla, Phosphoric acid, Propionic acid, Sodium propionate or mixture thereof The sweetening agent can be selected from a group comprising Acesulfame Potassium, Alitame, Aspartame, Dextrose, Erythritol, Fructose, Glucose Liquid, Glycerin, Inulin, Isomalt, Lactitol, Maltitol, Maltitol Solution, Maltose, Mannitol, NeohesperidinDihydrochalcone, Neotame, Saccharin, Saccharin Sodium, Sodium Cyclamate, Sorbitol, Sucralose, Sucrose, Compressible Sugar, Confectioner's Sugar, Tagatose, Thaumatin, Trehalose, Xylitol or mixture thereof The Antiadherent can be selected from a group comprising Magnesium stearate, Calcium Stearate, Leucine, Colloidal Silicon Dioxide, Talc, Starch, Cellulose Microcrystalline, Leucine or mixture thereof The Polymers can be selected from a group comprising hydroxypropyl methylcellulose, polyethylene glycol, hydroxypropyl cellulose and its derivative, polysorbate, Soluplus® (polyvinyl caprolactam-polyvinyl acetate-polyethylene), sodium carboxy methyl cellulose, Talc, Titanium dioxide, simethicon, Eudragit, purified water and colorant. The polymers can be used in the film coating material or as excipient, can be present in a concentration of from about 1% to about 5% by weight of the total weight of the composition.

The Surfactants can be selected from a group comprising anionic surfactants such as sodium lauryl sulfate and docusate sodium, cationic surfactants such as cetrimide, ampholytic surfactants such as N-dodecyl-N, N-dimethylbetaine, non-ionic surfactants such as sorbitan fatty acid esters, polysorbates, polyoxyethylene alkyl ethers, poloxamers, medium-chain triglycerides, polyoxylglycerides, polyoxyethylene castor oil derivatives and combinations thereof. The surfactants can be present in a concentration of from about 0% to about 5% by weight of the total weight of the composition.

The Anti-dusting agents are Edible oils.

The Adsorbents can be selected from a group comprising Bone Gelatin (Type B), Skin Gelatin (Type A) or mixture thereof. Gelatine also works as suspending agent.

The solubilizer or emulsifier or dispersing agent can be selected from a group comprising Tween 80, Labrasol, HPMC, DOSS, caproyl 909, labrafac, labrafil, peceol, transcutol, Capmul MCM, Capmul PG-12, Captex 355, gelucire, lecithine, vitamin E TOPS or other acceptable solubilizer, emulsifier or dispersing agents.

The Solvent can be selected from a group comprising purified water, Water for Injection, Arometic water, Alcohol, Glycerol, Propylene Glycol USP, Ether (Diethyl ether), Polyethylene glycol and derivatives, Diethlyene glycol monemethyl ether and its derivative, Dimethylacetamide, Fixed oil form plant source or mixture thereof.

The Wetting agents can be selected from a group comprising Benzalkonium Chloride, Benzethonium chloride, Cetylpyridinium Chloride, Docusate Sodium, Glycine, Glycofurol, Hypromellose, Poloxamer, Phospholipids, Polyoxyethylene Alkyl Ethers, Polyoxyethylene Castor Oil Derivatives, PolyoxyethyleneSorbitan Fatty Acid Esters, Polyoxyethylene Stearates, Sodium Lauryl Sulfate, Sorbitan Esters (Sorbitan Fatty Acid Esters), Tricaprylin or mixture thereof.

The Buffering agent can be selected from a group comprising Adipic Acid, Ammonia solution, Boric Acid, Calcium Carbonate, Calcium hydroxide, Calcium Lactate, Calcium Phosphate (Tribasic), Citric Acid Monohydrate, Dibasic sodium phosphate, Diethanolamine, Glycine, Maleic Acid, Malic Acid, Methionine, Monosodium Glutamate, Monoethanolamine, Monosodium glutamate, Potassium Citrate, Sodium Acetate, Sodium Borate, Sodium Carbonate, Sodium Citrate Dihydrate, Sodium Hydroxide, Sodium Lactate, Sodium Phosphate (Dibasic), Sodium Phosphate (Monobasic), Propionic Acid, Phosphoric acid, Sodium bicarbonate, Triethanolamine or mixture thereof.

The Suspending Agents can be selected from a group comprising Acacia, Agar, Alginic Acid, Bentonite, Carbomer, Calcium stearate, Carboxymethylcellulose Calcium, Carboxymethylcellulose Sodium, Carrageenan, Microcrystalline cellulose, Carboxymethylcellulose Sodium, Cellulose Powdered, Ceratonia, Colloidal Silicon Dioxide, Dextrin, Gelatin, Guar Gum, Hydrophobic Colloidal Silica, Hydroxyethyl Cellulose, Hydroxyethylmethyl Cellulose, Hydroxypropyl Cellulose, Hypromellose, Kaolin, Magnesium Aluminum Silicate, Maltitol Solution, Medium-chain Triglycerides, Methylcellulose, Phospholipids, Polycarbophil, PolyoxyethyleneSorbitan Fatty Acid Esters, Potassium Alginate, Povidone, Propylene Glycol Alginate, Sodium Alginate, Saponite, Sesame oil, Sorbitan Esters (Sorbitan Fatty Acid Esters), Sucrose, Tragacanth, Vitamin E Polyethylene Glycol Succinate, Xanthan Gum, Ceratonia, Hectorite or mixture thereof.

The Viscosity-modifying Agents can be selected from a group comprising Acacia, Agar, Alginic Acid, Bentonite, Carboxymethylcellulose Calcium, Carboxymethylcellulose Sodium, Carrageenan, Ceratonia, Cetostearyl Alcohol, Chitosan, Colloidal Silicon Dioxide, Cyclomethicone, Ethylcellulose, Gelatin, Glycerin, GlycerylBehenate, Guar Gum, Hectorite, Hydrophobic Colloidal Silica, Hydroxyethyl Cellulose, Hydroxyethylmethyl Cellulose, Hydroxypropyl Cellulose, Hydroxypropyl Starch, Hypromellose, Magnesium Aluminum Silicate, Maltodextrin, Methylcellulose, Myristyl Alcohol, Polydextrose, Poly(methyl vinyl ether/maleic anhydride), Polyvinyl Alcohol, Propylene Glycol, Propylene Glycol Alginate, Saponite, Sodium Alginate, Sodium chloride, Starch, Sulfobutylether b-Cyclodextrin, Tragacanth, Xanthan Gum or mixture thereof.

The Preservatives can be selected from a group comprising Alcohol, Benzalkonium Chloride, Benzethonium Chloride, Benzoic Acid, Benzyl Alcohol, Boric Acid, Bronopol, Butylene Glycol, Butylatedhydroxyanisole, Butylparaben, Calcium Acetate, Calcium Chloride, Calcium Lactate, Cetrimide, CetylpyridiniumChloride, Chlorhexidine, Chlorobutanol, Chlorocresol, Chloroxylenol, Citric Acid Monohydrate, Cresol, Dimethyl ether, Ethylparaben, Glycerin, Hexetidine, Imidurea, Isopropyl alcohol, lactic acid, Methylparaben, Monothioglycerol, Pentetic Acid, Phenol, Phenoxyethanol, Phenylethyl Alcohol, Phenylmercuric Acetate, Phenylmercuric Borate, Phenylmercuric Nitrate, Potassium Benzoate, Potassium Metabisulfite, Potassium Sorbate, Propionic Acid, Propylene Glycol, Propyl gallate, Propylparaben, Propylparaben Sodium, Sodium Acetate, Sodium Benzoate, Sodium Borate, Sodium Lactate, Sodium Metabisulfite, Sodium Propionate, Sodium Sulfite, Sorbic Acid, Sulfur Dioxide, Thimerosal, Sulfobutyletherb-cyclodextrin, Xylitol, Edetic acid or mixture thereof.

The Antioxidants can be selected from a group comprising Alpha/beta/delta/gamma tocopherols, Ascorbic Acid, AscorbylPalmitate, ButylatedHydroxyanisole, ButylatedHydroxytoluene, Citric Acid Monohydrate, Erythorbic Acid, Ethyl oleate, Fumaric Acid, Malic Acid, Methionine, Potassium Metabisulfite, Propionic Acid, Propyl Gallate, Sodium Ascorbate, Sodium Formaldehyde Sulfoxylate, Sodium Metabisulfite, Sodium Sulfite, Sodium Bisulfite, Sodium Thiosulfate, Sulfur Dioxide, Thymol, Vitamin E Polyethylene Glycol Succinate, Monothoglycerol, Phosphoric acid or mixture thereof.

The Tonicity adjusting agent can be selected from a group comprising Dextrose, Glycerin, HydroxypropylBetadex, Mannitol, Potassium Chloride, Sodium Chloride or mixture thereof.

The humectant can be selected from a group comprising Ammonium Alginate, Butylene Glycol, Cyclomethicone, Glycerin, Polydextrose, Propylene Glycol, Sodium Hyaluronate, Sodium Lactate, Sorbitol or mixture thereof.

Dicom DC SP®, F-Melt Type C® etc are used as excipients.

In one of the preferred embodiments of the present invention a pharmaceutical composition comprising Levocloperastine or pharmaceutically acceptable salt thereof, wherein the composition is a tablet composition comprising Levocloperastine 1-5%, diluent 20-80%, disintegrant 1-10%, binder 0.5-5%, lubricant 0.2-2%, glidant 0-2% and surfactant 0-5%, by total weight of the tablet composition.

In one of the preferred embodiments of the present invention a pharmaceutical composition comprising Levocloperastine or pharmaceutically acceptable salt thereof, wherein the composition is a solution composition comprising Levocloperastine 1-5%, anti-oxidant 1-10% and preservative 0.01-10% by total weight of the solution composition, and further comprising buffer, and optionally flavouring and sweetening agent.

In other embodiments of the present invention a pharmaceutical composition comprising Levocloperastine or pharmaceutically acceptable salt thereof, wherein the composition is a hard gel capsule composition, comprising Levocloperastine, surfactant, binder, polymer, diluent, and solvent.

In other embodiments of the present invention a pharmaceutical composition comprising Levocloperastine or pharmaceutically acceptable salt thereof, wherein the composition is a soft gel capsule composition, comprising Levocloperastine, solubilizer, stabilizer, lubricant, and optionally other excipients.

The pharmaceutical composition described herein may be prepared by conventional technology well known to those skilled in the art such as wet granulation, dry granulation and direct compression and the like.

In one of the preferred embodiments, present invention is to provide a process for preparation of a stable pharmaceutical composition comprising Levocloperastine or its pharmaceutically acceptable salt thereof and one or more pharmaceutical acceptable excipients comprising following steps:

1) Mixing Levocloperastine or its salt with diluent and disintegrants to obtain a blend.
2) Disperse binder in solvent under stirring to obtain a binder solution.
3) Granulate the blend obtained in step 1 in a granulator with binder solution to obtain wet granules. Dry the wet granules.
4) Size the dried granules and add desired amount of lubricant to obtain a lubricated granule.
5) Compress the lubricated granules of step 6 to obtain compressed tablets.
6) Optionally, coat the compressed tablets using coating solution.

In one of the preferred embodiments, present invention is to provide a process for preparation of a stable pharmaceutical composition comprising Levocloperastine or its pharmaceutically acceptable salt thereof and one or more pharmaceutical acceptable excipients comprising following steps:

1) Mixing Levocloperastine or its salt with diluent and disintegrants to obtain a blend.
2) Disperse binder in solvent under stirring to obtain a binder solution.
3) Granulate the blend obtained in step 1 in a granulator with binder solution to obtain wet granules. Dry the wet granules.
4) Size the dried granules and add desired amount of lubricant to obtain a lubricated granule.
5) Fill the lubricated granule into the suitable sized capsule.

In one of the preferred embodiments, present invention is to provide a process for preparation of a stable pharmaceutical composition comprising Levocloperastine or its pharmaceutically acceptable salt thereof and one or more pharmaceutical acceptable excipients comprising following steps:

1) Mixing Levocloperastine or its salt with diluent and disintegrants to obtain a blend.
2) Mixing remaining excipients to obtained blend
3) Mixing blend of step 1 to the blend of step 2
4) Compress the dry blend to obtained tablet or fill into the capsule.
5) optionally coating the compress tablets.

In one of the preferred embodiments, present invention is to provide a process for preparation of a stable pharmaceutical composition comprising Levocloperastine or its pharmaceutically acceptable salt thereof and one or more pharmaceutical acceptable excipients wherein said Levocloperastine is mixed with suitable pharmaceutically acceptable excipients and filled in to soft gel capsule.

In one of the preferred embodiment, present invention is to provide a process for preparation of a stable pharmaceutical composition comprising Levocloperastine or its pharmaceutically acceptable salt thereof and one or more pharmaceutical acceptable excipients wherein said Levocloperastine or its pharmaceutically acceptable salt thereof undergoes a size reduction process and adding buffer, suspending agent, antioxidant, preservative, co solvent, preservative, sweetening agent or flavouring agent to obtain suspension dosage from.

In one of the preferred embodiments, present invention is to provide stable pharmaceutical composition comprising Levocloperastine or its pharmaceutically acceptable salt thereof and one or more pharmaceutical acceptable excipients, wherein the content uniformity of the said composition is in between 95% and 105%.

In one of the preferred embodiments, present invention is to stable pharmaceutical composition comprising Levocloperastine or its pharmaceutically acceptable salt thereof and one or more pharmaceutical acceptable excipients, wherein the dissolution rate of Levocloperastine is not less than 90% at 45 minutes when the composition is subjected to the dissolution test using paddle method at a rotation of 50 rpm in 900 ml of purified water.

In yet another embodiment, the present invention is to provide a stable pharmaceutical composition comprising Levocloperastine and one or more pharmaceutically acceptable excipients, wherein the said composition is in the form of tablet, capsule, solution or suspension, and the said composition can be used as single dose or multi dose administration formulation in adult as well as paediatric patients for the treatment of Vertigo, Peripheral vertigo, Meniere's disease and giddiness.

EXAMPLES

One or more general or specific embodiments are further described in detail in the following examples, which are not intended, in any way, to limit the scope of the invention to the specifically disclosed embodiments only. It is readily apparent to those of ordinary skill in the art in light of the teachings of this invention that certain changes and modifications may be made thereto without departing from the scope of the invention.

Example-1: Levocloperastine Tablet

| Sr. No. | Ingredients | % w/w |
|---|---|---|
| 1 | levocloperastine | 1-5 |
| 2 | Diluent | 20-80 |
| 3 | Disintegrant | 1-10 |
| 4 | Binder | 0.5-5 |
| 5 | Lubricant | 0.2-2 |
| 6 | Glidant | 0-2 |
| 7 | Surfactant | 0-5 |
| 8 | Solvent | Qs |
| 9 | Film Coating material | 1-5 |

Process of Preparation of Tablet:

1. Levocloperastine was mixed with diluent and disintegrants to obtain a blend.
2. The binder was dispersed in the solvent under stirring to obtain a binder solution.
3. The blend obtained in step 1 was granulated in granulator with the binder solution.
4. The wet granules were dried in fluid bed dryer then sieved the dried granules.
5. The granules were mixed with the lubricant and compressed into tablets and coated with the coating solution prepared by dissolving the film coating material in the solvent.

Example-2: Levocloperastine Hard Gel Capsule

| Sr. No | Ingredient | % (w/w) |
|---|---|---|
| 1. | Levocloperastine Fendizoate | 35 |
| 2. | Sodium Lauryl Sulfate | 0.5-2.5 |
| 3. | Polyvinylpyrrolidone | 0.5-25.0 |
| 4. | Vinylpyrrolidone-vinyl acetate copolymer | 0.5-5.0 |
| 5. | Polysorbate 80 | 1-15 |
| 6. | Silicified MCC | 0-5.0 |
| 7. | Lactose Monohydrate + Maize Starch | 0-2.0 |
| 8. | Ethanol | Q.S. |

Process of Preparation of Capsule:

1. Levocloperastine Fendizoate was mixed with lactose monohydrate, maize starch, vinylpyrrolidone-vinyl acetate copolymer rand silicified MCC to obtain a blend.
2. Polyvinylpyrrolidone was dispersed in solvent under stirring to obtain a binder solution.
3. The blend obtained in step 1 was granulated in the granulator with the binder solution.
4. The wet granules were dried in fluid bed dryer then sieved the dried granules.
5. The granules were mixed with sodium lauryl sulfate and polysorbate 80, and filled in capsules.

Example-3: Levocloperastine Soft Gel Capsule

| Sr. No. | Ingredients | mg per capsule |
|---|---|---|
| 1 | Levocloperastine Fendizoate | 35 |
| 2 | Labrafac | 15 |
| 3 | Polyoxyl castor oil | 15 |
| 4 | Lecithine | 20 |
| 5 | Gelatine | 20 |

Levocloperastine Fendizoate and the excipients as per above table were mixed and filled in a soft gel capsule.

Example-4: Levocloperastine Solution

| Sr. No. | Ingredients | % w/w |
|---|---|---|
| 1 | Levocloperastine | 1-5 |
| 2 | Buffer | Q.S. to adjust pH 4.0 to 8.0 |
| 3 | Anti-oxidant | 0-10 |
| 4 | Preservative | 0.01-10 |
| 5 | Co solvent | 0.01-50 |
| 6 | Sweetening agent | 0.01-5.0 |
| 7 | Flavoring agent | 0.01-5.0 |
| 8 | Water | Q.S. |
| Amount of solution | | 100 |

Process of Preparation of Solution:

1. Take purified water in SS vessels.
2. Add preservative, buffer, sweetening agent, and anti-oxidant to it and stir up to uniform mix.
3. Add Levocloperastine, flavoring agent, and co-solvent; and stir up to uniform mix.
4. Make up final volume by purified water.

Example-5: Levocloperastine Suspension

| Sr. No. | Ingredients | % w/w |
|---|---|---|
| 1 | Levocloperastine | 1-5 |
| 2 | Buffer | To make pH 4.0 to 8.0 |
| 3 | Suspending agent | 0.01-10 |
| 4 | Flocculating agent | 0.01-10 |
| 5 | Anti-oxidant | 0-10 |
| 6 | Preservative | 0.01-10 |
| 7 | Co solvent | 0.01-50 |
| 8 | Preservative | 0.01-10 |
| 9 | Sweetening agent | 0.01-5.0 |
| 10 | Flavouring agent | 0.01-5.0 |
| 11 | Water | Q.S. |
| Amount of suspension | | 100 |

Process of Preparation of Suspension:

1. Take 60% of purified water in SS vessels.
2. Add preservative, buffer, sweetening agent, anti-oxidant, suspending agent and flocculating agent, and stir up to uniform mix.
3. Add Levocloperastine and stir up to uniform mix.
4. Add flavoring agent and co-solvent and stir up to uniform mix.

5. Make up final volume by purified water.

Example-6: Levocloperastine Capsule

| Sr. No. | Ingredients | Qty./Unit |
|---|---|---|
| 01 | Levocloperastine Fendizoate | 20.0-35.0 mg |
| 02 | Soluplus ® (polyvinyl caprolactam-polyvinyl acetate-polyethylene) | 30-45 mg |
| 03 | Dimethylacetamide | 0.1-0.3 mL |
| 04 | Dicom DC SP ® | 230-260 mg |
| 05 | Talc Powder | 1-3 mg |
| 06 | Magnesium Stearate | 1-3 mg |

Process for Preparation of Capsule: Wet Granulation Method

1. Dimethylacetamide and Soluplus® were stirred in a glass vessel.
2. Levocloperastine Fendizoate was added and stirred up to uniform mix.
3. Dicom DC SP® was sifted through #40 sieve and added to above mix and stirred up to uniform mix.
4. The mix was granulated in a granulator.
5. The granules were dried in hot air oven at 50° C.
6. The dried granules were sifted through #40 sieve, and mixed with talc powder (sifted through #80 sieve) and magnesium stearate (sifted through #80 sieve).
7. The obtained mix was filled in Size '0' capsule Example-7: Levocloperastine Capsule

| Sr. No. | Ingredients | Qty./Unit |
|---|---|---|
| 01 | Levocloperastine Fendizoate | 20.0 mg |
| 02 | Dicom DC SP | 227.0 mg |
| 03 | Talc Powder | 2.0 mg |
| 04 | Magnesium Stearate | 1.0 mg |

Process for Preparation of Capsule: Dry Mix Method

Dicom DC SP® (sifted through #40 sieve), Levocloperastine Fendizoate (sifted through #40 sieve), talc powder (sifted through #80 sieve) and magnesium stearate (sifted through #80 sieve) were blended in a blender up to uniform mix; and filled in Size '0' capsule.

Example-8: Levocloperastine Tablet

| Sr. No. | Ingredients | Qty./Unit |
|---|---|---|
| 01 | Levocloperastine Fendizoate | 20.0 mg |
| 02 | F-Melt Type C ® | 94.6 mg |
| 03 | Crosscarmellose Sodium | 10.0 mg |
| 04 | Magnesium Stearate | 5.0 mg |

Process for Preparation of Tablet: Dry Mix Method

F-Melt Type C® (sifted through #40 sieve), Levocloperastine Fendizoate (sifted through #40 sieve), Crosscarmellose Sodium (sifted through #40 sieve) and magnesium stearate (sifted through #80 sieve) were blended in a blender up to uniform mix; and compressed in 8/32 or 9/32 concave punch.

Example-9: Levocloperastine HCl Solution (20 mg/0.1 mL)

| Sr. No. | Ingredients | mg/0.1 mL |
|---|---|---|
| 01 | Levocloperastine Hydrochloride | 20.0 mg |
| 02 | Polyethylene Glycol 300 | 30.0 mg |
| 03 | Polypropylene glycol | 10.0 mg |
| 04 | Glycerin | 0.1 mg |
| 05 | Hydroxypropyl Methylcellulose E15 | 0.1 mg |
| 06 | Purified Water | Q.S to 0.1 mL |

Process for Preparation of Levocloperastine HCl Solution

1. About 20% of total required quantity of purified water was taken in a glass vessel and Polyethylene Glycol 300, Polypropylene glycol were added and stirred up to uniform mix.
2. Levocloperastine HCl was added and stirred up to uniform mix.
3. Glycerin and Hydroxypropyl methylcellulose E15 were added and stirred up to uniform mix.
4. Final volume was made-up by purified water.

Example-10: Levocloperastine HCl Solution (20 mg/0.1 mL)

| Sr. No. | Ingredients | mg/0.1 mL |
|---|---|---|
| 01 | Levocloperastine Hydrochloride | 20.0 mg |
| 02 | M- Polyethylene Glycol 350 | 30.0 mg |
| 03 | Polypropylene glycol | 6.0 mg |
| 04 | Polyethylene Glycol 400 | 17.0 mg |
| 05 | Dehydrated Alcohol | 7.0 mg |
| 06 | Purified Water | Q.S to 0.1 mL |

Process for Preparation of Levocloperastine HCl Solution

1. About 10% of total required quantity of purified water was taken in a glass vessel and Polyethylene Glycol 400, Polypropylene glycol, Dehydrated Alcohol and M-Polyethylene Glycol 350 were added and stirred up to uniform mix.
2. Levocloperastine HCl was added and stirred up to uniform mix.
3. Final volume was made-up by purified water.
4. The solution was filtered through 0.45 Nylon filter.

Example-11: Treatment of Peripheral Vertigo

The current study was designed as an open label, two-treatment arm, active comparator controlled, Clinical trial in patients with Peripheral vertigo. This study involved a screening phase, randomization and treatment phase as mentioned below:

Screening phase (Visit 1): −14 to −1 day
Baseline visit and day of randomization (Visit 2): Day 0/1
Treatment phase: Day 1 to Day 28
End of treatment (Visit 4): Day 29±2 days Patients with Peripheral vertigo, meeting the mentioned eligibility criteria were identified and shortlisted patients underwent screening within 14 days prior to randomization. A total of 16 patients were randomized in the ratio of 3:1 to receive the test and active comparator products (12 patients received test product and 4 patients received active comparator product). Test product was consumed as 20 mg Levocloperastine orally three times a day for 28 days. Active comparator (standard of care) was consumed by the patients as per the investigator's sole discretion and medical judgement. The standard of care treatment included Betahistine 16 mg tablets three times daily OR Betahistine 16 mg tablets three times daily plus Acetazolamide 125 mg tablets two time daily OR Cinnarizine 25 mg tablets three times daily which was given to patient.

MVS Score: Mean change in MVS score from baseline score was compared between two treatment arms. The absolute data and mean changes from baseline data are presented in Table 1:

TABLE 1

| MVS Score | Test treatment<br>Mean ± SD (Min, Max) | Standard of care<br>Mean ± SD (Min, Max) |
|---|---|---|
| Baseline (Day 0/1) | 2.2 ± 0.29 (1.7, 2.8) | 2.2 ± 1.4 (2.1, 2.4) |
| Interim visit [Day 7 + 3] | 1.5 ± 0.49 (1.1, 2.8) | 1.7 ± 0.35 (1.3, 2.1) |
| Change from baseline | −0.7 ± 0.33 (−1.1, 0.0) | −0.5 ± 0.33 (−0.9, −0.2) |
| Change as % | 31.81% | 22.72% |
| A/28 Days [Day 29 ± 2] | 1.1 ± 0.58 (0.3, 2.2) | 1.1 ± 0.35 (0.7, 1.5) |
| Change from baseline | −1.1 ± 0.45 (−1.8, −0.3) | −1.1 ± 0.35 (−1.5, −0.8) |
| Change as % | −50.00% | −50.00% |

Levocloperastine is found to be equally efficacious in comparison to standard of care treatment with regards to primary efficacy endpoint i.e. MVS score and similar trend while evaluating other co secondary endpoints, NVI score, THI severity & IGA as well.

Additionally, mean change in composite score of vegetative concomitant symptoms from baseline score was compared between two treatment arms. The absolute data and mean changes from baseline data are presented below in Table 2.

Score of Vegetative Concomitant Symptoms

TABLE 2

| Data presentation | | Test treatment (N = 12) | Standard of care (N = 4) |
|---|---|---|---|
| Baseline | | | |
| Absolute data | Mean ± SD | 1.3 ± 1.05 | 1.6 ± 0.81 |
| | (Min, Max) | (0.0, 4.0) | (0.0, 3.0) |
| 7 days after treatment onset [Interim visit: Day 7 + 3] | | | |
| Absolute data | Mean ± SD | 0.6 ± 0.73 | 1.2 ± 0.91 |
| | (Min, Max) | (0.0, 2.0) | (0.0, 3.0) |
| Change from baseline | Mean ± SD | −0.6 ± 0.81 | −0.4 ± 0.50 |
| | (Min, Max) | (−3.0, 1.0) | (−1.0, 0.0) |
| | Change as % | −46.15 | −25.00 |
| 28 days after treatment onset [end of treatment: Day 29 ± 2] | | | |
| Absolute data | Mean ± SD | 0.2 ± 0.47 | 0.6 ± 0.63 |
| | (Min, Max) | (0.0, 2.0) | (0.0, 2.0) |
| Change from baseline | Mean ± SD | −1.1 ± 0.98 | −1.0 ± 0.52 |
| | (Min, Max) | (−3.0, −1.0) | (−2.0, 0.0) |
| | Change as % | −84.62 | −62.50 |

Study Data confirms that Levocloperastine is able to control vegetative concomitant symptoms more rapidly and more significant way compared to existent standard of care therapy. Levocloperastine is statistically better in alleviating the vegetative concomitant symptoms than the standard of care treatment even though both the treatment showed clinical improvement.

Further, as shown statistically in table 1 and 2 within shorter duration of time drug is acting more superior than standard of care. The study shows favourable response and well tolerability in all patients. Levocloperastine is found to be equally efficacious in comparison to standard of care treatment.

The invention claimed is:

1. A method of treatment of vertigo, one or more symptoms of vertigo, or a disease associated with vertigo in a human subject, wherein the method comprises administering to the subject a therapeutically effective amount of levocloperastine or a pharmaceutically acceptable salt thereof.

2. The method according to claim 1, wherein the one or more symptoms of vertigo or the disease associated with vertigo are selected from the group consisting of Peripheral Vertigo, Meniere's disease, Tinnitus, Hearing loss, Giddiness, Dysesthesia of motion and position, Nystagmus, Dysequilibrium, Dizziness, Head deviation, Nausea, Vomiting, Sweating, Salivation and Tachycardia, Dysstasia and Walking unsteadiness, Staggering, Rotary sensation, Tendency to fall, Lift sensation, Blackout, Change of position (lying), Bowing, Getting up, driving, Head movements (inclination, twist), and eye movement.

3. The method according to claim 1, wherein levocloperastine or a pharmaceutically acceptable salt thereof is administered at a daily dose of about 10-1000 mg.

4. The method according to claim 3, wherein levocloperastine or a pharmaceutically acceptable salt thereof is administered at a daily dose of about 10-100 mg.

5. The method according to claim 4, wherein levocloperastine or a pharmaceutically acceptable salt thereof is administered at a daily dose of about 10-80 mg.

6. The method according to claim 1, wherein levocloperastine or a pharmaceutically acceptable salt thereof is administered in an amount from about 60-90 mg once daily, or about 30-45 mg twice a day, or about 20-30 mg thrice a day.

7. The method according to claim 1, wherein levocloperastine or a pharmaceutically acceptable salt thereof is administered in an amount of from about 70-120 mg once daily, or about 35-60 mg twice a day, or about 25-40 mg thrice a day.

8. The method according to claim 1, wherein levocloperastine or a pharmaceutically acceptable salt thereof is administered in an amount from about 90-160 mg once daily, or about 45-80 mg twice a day, or about 30-55 mg thrice a day.

9. The method according to claim 1, wherein levocloperastine or a pharmaceutically acceptable salt thereof is administered in an amount of from about 20-30 mg three times a day.

10. The method according to claim 1, wherein levocloperastine or a pharmaceutically acceptable salt thereof is administered in an amount of from about 30-55 mg three times a day.

11. The method according to claim 1, wherein levocloperastine is administered for a duration of the treatment that is shorter as compared to the standard of care therapy.

12. The method according to claim 11, wherein the standard of care therapy is selected from one or more of betahistine 16 mg tablets three times daily or betahistine 16 mg tablets three times daily plus acetazolamide 125 mg tablets two time daily or cinnarizine 25 mg tablets three times daily.

13. The method according to claim 1, wherein levocloperastine or a pharmaceutically acceptable salt is administered in a pharmaceutical composition.

14. The method according to claim 13, wherein the pharmaceutical composition is an oral composition.

15. The method according to claim 14, wherein the oral composition a tablet, capsule, granules, powder, solution, syrup, emulsion or suspension composition.

* * * * *